United States Patent
Schubert et al.

(10) Patent No.: US 9,110,084 B2
(45) Date of Patent: Aug. 18, 2015

(54) CARTRIDGE DEVICE FOR A MEASURING SYSTEM FOR MEASURING VISCOELASTIC CHARACTERISTICS OF A SAMPLE LIQUID, A CORRESPONDING MEASURING SYSTEM, AND A CORRESPONDING METHOD

(71) Applicant: C A CASYSO AG, Muttenz (CH)

(72) Inventors: Axel Schubert, Munich (DE); José Javier Romero-Galeano, Markt Schwaben (DE); Max Kessler, Munich (DE)

(73) Assignee: C A Casyso AG, Basel (CH)

( * ) Notice: Subject to any disclaimer, the term of this patent is extended or adjusted under 35 U.S.C. 154(b) by 0 days.

(21) Appl. No.: 13/894,998

(22) Filed: May 15, 2013

(65) Prior Publication Data
US 2013/0323846 A1 Dec. 5, 2013

Related U.S. Application Data

(63) Continuation of application No. 12/640,376, filed on Dec. 17, 2009, now Pat. No. 8,448,499.

(60) Provisional application No. 61/140,344, filed on Dec. 23, 2008.

(51) Int. Cl.
*G01N 11/14* (2006.01)
*G01N 33/86* (2006.01)
*G01N 33/49* (2006.01)

(52) U.S. Cl.
CPC ............... *G01N 33/86* (2013.01); *G01N 11/14* (2013.01); *G01N 33/4905* (2013.01)

(58) Field of Classification Search
CPC .................................................. G01N 11/14
USPC ............ 73/54.28, 54.33, 54.35, 64.41–64.43, 73/64.53; 356/39; 422/73; 436/69
See application file for complete search history.

(56) References Cited

U.S. PATENT DOCUMENTS 3,714,815 A 2/1973 Hartert et al.
3,803,903 A * 4/1974 Lin .............................. 73/54.31
(Continued)

FOREIGN PATENT DOCUMENTS

CN 101195112 6/2006
DE 27 40 932 11/1978
(Continued)

OTHER PUBLICATIONS

Greilich et al., "Near-site monitoring of the antiplatelet drug abciximab using the Hemodyne analyzer and modified thrombelastograph," J Cardiothorac Vasc Anesth., 13(1):58-64, Feb. 1999.
(Continued)

*Primary Examiner* — Hezron E Williams
*Assistant Examiner* — Hoang Nguyen
(74) *Attorney, Agent, or Firm* — Fish & Richardson P.C.

(57) ABSTRACT

The present invention is directed to a cartridge device for a measuring system for measuring viscoelastic characteristics of a sample liquid, in particular a blood sample, comprising a cartridge body having at least one measurement cavity formed therein and having at least one probe element arranged in said at least one measurement cavity for performing a test on said sample liquid; and a cover being attachable on said cartridge body; wherein said cover covers at least partially said at least one measurement cavity and forms a retaining element for retaining said probe element in a predetermined position within said at least one measurement cavity. The invention is directed to a measurement system and a method for measuring viscoelastic characteristics of a sample liquid.

18 Claims, 11 Drawing Sheets

(56) References Cited

U.S. PATENT DOCUMENTS

| | | | |
|---|---|---|---|
| 3,903,903 A * | 9/1975 | Matsumura | 132/201 |
| 4,148,216 A * | 4/1979 | Do et al. | 73/54.26 |
| 4,193,293 A * | 3/1980 | Cavallari | 73/54.41 |
| 4,319,194 A | 3/1982 | Cardinal | |
| 4,726,220 A * | 2/1988 | Feier et al. | 73/54.34 |
| 4,753,776 A | 6/1988 | Hillman et al. | |
| 4,756,884 A | 7/1988 | Hillman et al. | |
| 4,765,180 A | 8/1988 | Clifton | |
| D302,294 S | 7/1989 | Hillman | |
| 4,868,129 A | 9/1989 | Gibbons et al. | |
| 4,948,961 A | 8/1990 | Hillman et al. | |
| 4,963,498 A | 10/1990 | Hillman et al. | |
| 5,028,142 A | 7/1991 | Ostoich et al. | |
| 5,077,017 A | 12/1991 | Gorin et al. | |
| 5,104,813 A | 4/1992 | Besemer et al. | |
| 5,164,598 A | 11/1992 | Hillman et al. | |
| 5,207,988 A | 5/1993 | Lucas | |
| 5,222,808 A | 6/1993 | Sugarman et al. | |
| 5,223,219 A | 6/1993 | Subramanian et al. | |
| 5,287,732 A | 2/1994 | Sekiguchi | |
| D347,067 S | 5/1994 | Shartle et al. | |
| 5,447,440 A | 9/1995 | Davis et al. | |
| 5,531,102 A | 7/1996 | Brookfield et al. | |
| 5,777,212 A | 7/1998 | Sekiguchi et al. | |
| 5,777,215 A * | 7/1998 | Calatzis et al. | 73/64.41 |
| 5,902,937 A * | 5/1999 | Amrani et al. | 73/856 |
| 6,066,243 A | 5/2000 | Anderson et al. | |
| 6,200,532 B1 | 3/2001 | Wu et al. | |
| 6,537,819 B2 | 3/2003 | Cohen | |
| 6,613,286 B2 * | 9/2003 | Braun et al. | 422/554 |
| 6,662,031 B1 | 12/2003 | Khalil et al. | |
| 6,699,718 B1 | 3/2004 | Bruegger | |
| 6,838,055 B2 | 1/2005 | Sando et al. | |
| 6,951,127 B1 | 10/2005 | Bi | |
| 7,399,637 B2 * | 7/2008 | Wright et al. | 436/69 |
| 7,412,877 B1 * | 8/2008 | Bi | 73/54.28 |
| 7,491,175 B2 | 2/2009 | Ruether | |
| 7,595,169 B2 | 9/2009 | Swaim et al. | |
| 7,732,213 B2 | 6/2010 | Cohen et al. | |
| 7,745,223 B2 * | 6/2010 | Schubert et al. | 436/69 |
| 7,947,505 B2 | 5/2011 | Kawasaki et al. | |
| 8,110,392 B2 * | 2/2012 | Battrell et al. | 435/286.5 |
| 8,383,045 B2 * | 2/2013 | Schubert et al. | 422/73 |
| 8,448,499 B2 | 5/2013 | Schubert et al. | |
| 8,857,244 B2 | 10/2014 | Schubert et al. | |
| 2002/0081741 A1 * | 6/2002 | Braun et al. | 436/43 |
| 2003/0073244 A1 | 4/2003 | Cohen | |
| 2007/0059840 A1 | 3/2007 | Cohen et al. | |
| 2009/0130645 A1 | 5/2009 | Schubert et al. | |
| 2010/0154520 A1 | 6/2010 | Schubert et al. | |
| 2010/0184201 A1 | 7/2010 | Schubert et al. | |
| 2011/0237913 A1 | 9/2011 | Schubert et al. | |
| 2013/0323847 A1 | 12/2013 | Schubert | |
| 2013/0323848 A1 | 12/2013 | Schubert | |
| 2013/0333448 A1 | 12/2013 | Schubert | |

FOREIGN PATENT DOCUMENTS

| | | |
|---|---|---|
| DE | 10135569 | 2/2003 |
| EP | 0404456 | 12/1990 |
| EP | 1367392 A1 | 12/2003 |
| EP | 1394546 A1 | 3/2004 |
| EP | 1627725 | 2/2006 |
| EP | 1884778 | 2/2008 |
| GB | 2257256 | 1/1993 |
| WO | WO89/06803 A1 | 7/1989 |
| WO | WO 02/063273 | 8/2002 |
| WO | WO2005/106467 | 11/2005 |
| WO | WO 2006/091650 | 2/2006 |
| WO | WO 2006/126290 | 11/2006 |
| WO | WO2007047961 A2 | 4/2007 |
| WO | WO2008/093216 | 8/2008 |
| WO | WO2011/117017 | 2/2011 |

OTHER PUBLICATIONS

Khurana et al., "Monitoring platelet glycoprotein IIb/IIIa-fibrin interaction with tissue factor-activated thromboelastography," J Lab Clin Med., 130(4):401-411, Oct. 1997.

Nielsen et al., "Evaluation of the contribution of platelets to clot strength by thromboelastography in rabbits: the role of tissue factor and cytochalasin D," Anesth Analg., 91(1):35-39, Jul. 2000.

Prisco and Paniccia, "Point-of-Care Testing of Hemostasis in Cardiac Surgery", Thromb. J., vol. 1, No. 1, 10 pages, May 6, 2003.

International Search Report and Written Opinion for PCT/EP2011/051803, mailed Jul. 7, 2011, 11 pages.

International Preliminary Report on Patentability for PCT/EP2010/050454, issued Jul. 19, 2011, 4 pages.

Non-Final Office Action for U.S. Appl. No. 13/895,002 dated Dec. 20, 2013.

Calatzis et al., "Strategies to Assess Individual Susceptibility to abciximab Therapy Using a New Functional Assay," Annals of Hematology, (Berlin, DE) vol. 76, No. Suppl 1, 1998, p. A61, XP009097526.

Chakroun et al., "The influence of Fibrin Polymerizatino and Platelet-Mediated Contractile Forces on Citrated Whole Blood Thromboelstography Profile," Thrombosis and Haemostasis, May 2006, vol. 95, No. 5, pp. 822-828.

Hastert H: "Blood Coagulation Studies with Thromboelastography—A New Research Method," Klin Wochenschrift, 26:577-583, 1948—English translation.

Kawasaki et al., "The Effects of Vasoactive Agents, Platelet Agonists and Anticoagulation on Thrombelastography," ACTA Anaesthesiologica Scandinavica, Oct. 2007, vol. 51, No. 9, pp. 1237-1244.

Nield et al., "MRI-Based Blood Oxygen saturation measurements in infants and children with congenital heart disease," Pediatric Radiology (2002) 32:518-522.

Noon et al., "Reduction of Blood Trauma in Roller Pumps for Long-term Perfusion" World J. Surg. (9), 1985, pp. 65-71.

Novotny et al., "Platelets Secrete a Coagulation Inhibitor . . . ", Blood 1988 (72), pp. 2020-2025.

Rodzynek et al., "The Transfer Test: A New Screening Procedure for Thrombotic Diseases," The Journal of Surgical Research, Sep. 1983, vol. 35, No. 3, pp. 227-233.

Rotem Brochure—"When Minutes Count to Stop the Bleeding," Pentapharm GmbH, www.rotem.de, Jun. 2007.

Rugeri et al., "Diagnosis of Early Coagulation Abnormalities in Trauma Patients by Rotation Thrombelastography," Journal of Thrombosis and Haemostasis, Feb. 2007, vol. 5, No. 2, pp. 289-295.

Salooja et al., "Thrombelastography," Blood Coagulation & Fibrinolysis, vol. 12, No. 5, 2001, pp. 327-337.

Shore-Lesserson et al., " Thromboelastography-guided transfusion algorithm reduces tranfuslons in complex cardiac surgery," Anesthesia and Analgesia, Feb. 1999, vol. 88, No. 2, pp. 312-319.m.

Soria et al., "Fibrin Stabilizing Factor (F XIII) and Collagen Polymerization", Path. Biol. Suppl. 22 (86), 1974, pp. 1355-1357.

Spannagl et al., "Point-of-Care Analysis of the Hemostatic System," Laboratoriumsmedizin, (Kirchheim, DE), vol. 26, No. 1-2, Feb. 2002, pp. 68-76.

Srinivasa et al., "Thromboelastography: Where Is It and Where Is It Heading?" Int'l Anesthesiology Clinics, vol. 39, Iss. 1, Winter 2001, pp. 35-49.

Tanaka et al., "Thrombin Generation Assay and Viscoelastic Coagulation . . . " Anesthesia & Analgesia vol. 105, No. 4, Oct. 2007.

European Search Report for EP 07121222 dated Apr. 9, 2008.

European Search Report for EP 08172769 dated Jun. 4, 2009.

European Search Report for EP 09150740 dated Jun. 30, 2009.

International Search Report and Written Opinion for PCT/EP2010/050454 dated Apr. 20, 2010.

Office Action with Restriction/Election Requirement for U.S. Appl. No. 12/275,757 dated Sep. 15, 2010.

Non-Final Office Action for U.S. Appl. No. 12/275,757 dated Jan. 21, 2011.

Non-Final Office Action for U.S. Appl. No. 12/275,757 dated Oct. 18, 2011.

(56) References Cited

OTHER PUBLICATIONS

Non-Final Office Action for U.S. Appl. No. 12/688,306 dated Nov. 9, 2011.
Interview Summary for U.S. Appl. No. 12/275,757 dated Dec. 12, 2011.
Final Office Action for U.S. Appl. No. 12/688,306 dated Apr. 24, 2012.
Notice of Abandonment (per client) for U.S. Appl. No. 12/275,757 dated May 8, 2012.
Notice of Allowance for U.S. Appl. No. 12/688,306 dated Jul. 26, 2012.
Non-Final Office Action for U.S. Appl. No. 12/640,376 dated Aug. 15, 2012.
International Preliminary Report and Written Opinion for PCT/EP2011/051803 dated Sep. 25, 2012.
Notice of Allowance for U.S. Appl. No. 12/688,306 dated Nov. 1, 2012.
Notice of Allowance for U.S. Appl. No. 12/640,376 dated Jan. 29, 2013.
Non-Final Office Action for U.S. Appl. No. 12/764,611 dated Feb. 13, 2013.
Supplemental Notice of Allowance for U.S. Appl. No. 12/640,376 dated Feb. 28, 2013.
Chinese Office Action for Application No. 200980151858.5 dated Apr. 15, 2013.
Notice of Allowance for U.S. Appl. No. 12/764,611 dated Aug. 16, 2013.

* cited by examiner

CARTRIDGE DEVICE FOR A MEASURING SYSTEM FOR MEASURING VISCOELASTIC CHARACTERISTICS OF A SAMPLE LIQUID, A CORRESPONDING MEASURING SYSTEM, AND A CORRESPONDING METHOD

CROSS-REFERENCE TO RELATED APPLICATIONS

This application is a continuation of and claims priority to U.S. Ser. No. 12/640,376 filed Dec. 17, 2009, which claims the benefit of U.S. Provisional Application No. 61/140,344, filed Dec. 23, 2008, the entire disclosures of which are herein incorporated by reference.

FIELD OF THE INVENTION

The present invention relates to a cartridge device for a measuring system for measuring viscoelastic characteristics of a sample liquid, in particular of a blood sample liquid. The present invention also relates to a corresponding measuring system and method.

It is essential for survival that a wound stops bleeding, i.e. that the body possesses an adequate mechanism for haemostasis. The process of blood clotting can be activated in the case of injuries or inflammations by either extrinsic or intrinsic factors, e.g. tissue factor (TF) or Hagemann factor (F XII), respectively. Both activation channels are continued in a common branch of the cascade resulting in thrombin formation. The thrombin itself finally initiates the formation of fibrin fibres which represent the protein backbone of blood clots.

The other main constituent of the final blood clot are the thrombocytes which are interconnected by the fibrin fibres and undergo a number of physiological changes during the process of coagulation. Within limits a lack of thrombocytes can be substituted by an increased amount of fibrin or vice versa. This is reflected in the observation that the thrombocyte counts as well as the fibrinogen concentration varies even within a healthy population.

Various methods have been introduced to assess the potential of blood to form an adequate clot and to determine the blood clots stability. Common laboratory tests such as thrombocyte counts or the determination of fibrin concentration provide information on whether the tested component is available in sufficient amount but lack in answering the question whether the tested component works properly under physiological conditions (e.g. the polymerisation activity of fibrinogen under physiological conditions can not be assessed by common optical methods). Besides that, most laboratory tests work on blood-plasma and therefore require an additional step for preparation and additional time which is unfavourable especially under POC (point of care) conditions.

Another group of tests which overcomes these problems is summarized by the term "viscoelastic methods". The common feature of these methods is that the blood clot firmness (or other parameters dependent thereon) is continuously determined, from the formation of the first fibrin fibres until the dissolution of the blood clot by fibrinolysis. Blood clot firmness is a functional parameter, which is important for haemostasis in vivo, as a clot must resist blood pressure and shear stress at the site of vascular injury. Clot firmness results from multiple interlinked processes: coagulation activation, thrombin formation, fibrin formation and polymerization, platelet activation and fibrin-platelet interaction and can be compromised by fibrinolysis. Thus, by the use of viscoelastic monitoring all these mechanisms of the coagulation system can be assessed.

A common feature of all these methods used for coagulation diagnosis is that the blood clot is placed in the space between a cylindrical pin and an axially symmetric cup and the ability of the blood clot to couple those two bodies is determined.

The first viscoelastometric method was called "thrombelastography" (Hartert H: Blutgerinnungsstudien mit der Thrombelastographie, einem neuen Untersuchungsverfahren. Klin Wochenschrift 26:577-583, 1948). As illustrated in FIG. 1, in the thromboelastography, the sample as a sample liquid 1 is placed in a cup 2 that is periodically rotated to the left and to the right by about 5°, respectively. A probe pin 3 is freely suspended by a torsion wire 4. When a clot is formed it starts to transfer the movement of the cup 2 to the probe pin 3 against the reverse momentum of the torsion wire 4. The movement of the probe pin 3 as a measure for the clot firmness is continuously recorded and plotted against time. For historical reasons the firmness is measured in millimeters.

The result of a typical measurement of this kind is illustrated in FIG. 2. One of the most important parameters is the time between the activator induced start of the coagulation cascade and the time until the first long fibrin fibres have been build up which is indicated by the firmness signal exceeding a defined value. This parameter will be called clotting time or just CT in the following. Another important parameter is the clot formation time (CFT) which gives a measure for the velocity of the development of a clot. The CFT is defined as the time it takes for the clot firmness to increase from 2 to 20 mm. The maximum firmness a clot reaches during a measurement, further on referred to as maximum clot firmness or just MCF, is also of great diagnostic importance.

Modifications of the original thromboelastography technique (Hartert et al. (U.S. Pat. No. 3,714,815) have been described by Cavallari et al. (U.S. Pat. No. 4,193,293), by Do et al. (U.S. Pat. No. 4,148,216), by Cohen (U.S. Pat. No. 6,537.819). A further modification by Calatzis et al. (U.S. Pat. No. 5,777,215) illustrated in FIG. 3 is known under the term thromboelastometry.

Contrary to the modifications mentioned above, thromboelastometry is based on a cup 2 fixed in a cup holder 12 while the probe pin 3 is actively rotated. For this purpose the probe pin 3 is attached to a shaft 6 which is suspended by a ball bearing 7 in a base plate 11 and has a spring 9 connected to it. An oscillating motion perpendicular to the drawing plane induced at the opposite end of the spring is transformed into a periodically rotation of the shaft 6 and the connected cup 2 around a rotation axis 5 by about 5° in each direction. As the sample liquid 1 begins to coagulate the motion amplitude of the shaft 6 which is detected by the deflection of a light beam from detecting means 10 and a mirror 9 starts to decrease.

During coagulation the fibrin backbone creates a mechanical elastic linkage between the surfaces of the blood-containing cup 2 and a probe pin 3 plunged therein. A proceeding coagulation process induced by adding one or more activating factor(s) can thus be observed. In this way, various deficiencies of a patient's haemostatic status can be revealed and can be interpreted for proper medical intervention.

A general advantage of viscoelastometric, e.g. thromboelastometric, techniques compared to other laboratory methods in this field therefore is that the coagulation process and the change of mechanical properties of the sample are monitored as a whole. This means that—in contrary to other laboratory methods mentioned above—thromboelastometry does not only indicate if all components of the coagulation pathways are available in sufficient amounts but also if each component works properly.

To obtain detailed information on the correct amount and function of the thrombocytes as well as the fibrinogen and certain factors nowadays there is an increasing amount of compounds available which activate or inhibit certain components of the coagulation system. This allows determining at which point of the coagulation system a problem is located.

For practical reasons theses compounds are usually injected into the disposable plastic cup which later on is used for the measurement by using a pipette (either a manual or an automatic one). In the last preparation step, after the blood or plasma sample has been added, the whole amount of sample (blood/plasma and the additional chemicals) is mixed by drawing it into the pipette tip and dispensing it into the cup again.

The possibility to activate or to inhibit certain components of the coagulation system is especially useful in conjunction with state-of-the-art thromboelastometers such as the ROTEM (Pentapharm GmbH, Munich, Germany) which allows conducting four measurements in parallel. This allows detailed information on the current status of the coagulation-situation of a patient to be achieved and therefore allows an appropriate therapy within several minutes.

This is of particular importance in case of patients struck by massive blood loss as it often occurs in context with multiple traumata or major surgery. The blood of such patients often is diluted due to infusions which are administered to replace the loss in volume. This leads to a decrease of the concentration of thrombocytes as well as coagulation factors including fibrinogen.

Main advantages of thromboelastometry and thromboelastography are the possibility to perform several differential tests in parallel in order to precisely determine which kinds of blood products are the appropriate medication, the possibility to perform the measurement at or close to the point of care (POC) and—compared to other methods—the relatively small amount of time until valid results are available.

On the other hand the operator has to perform a significant number of steps in order to start the measurement (preparation of the reagents, attachment of the probe pin and the cup to the instrument, pipeting and mixing the blood sample and the reagents, adjustment of computer settings, etc.) on which the time spent is considerable, especially in the case of surgery being performed.

Furthermore this rather complex preparation also increases the risk of operating errors. There have been several approaches to simplify the usage of thromboelastometers. The Rotem-System (Pentapharm GmbH, Munich, Germany) e.g. is supplied with an automatic pipette which simplifies the handling to a large degree and thereby decreases the risk of operating errors.

WO 2008093216 describes the approach to provide the adequate amount of each of the reagents needed for one specific test in a ready-to-use mixture. In order to prevent the reaction of the reagents prior to the measurement, they are supplied in a lyophilisate state. This is additionally advantageous as the reagents can be stored at room temperature. Using this approach the preparation is reduced to the steps of adding the blood sample into the reagent container, mixing of blood with the reagent and transferring the mixture to the instrument.

US 2007/0059840 A1 describes a hemostasis analysis device and method. The device includes a container for holding a sample to be tested and a bobber configured to be buoyantly suspended on the sample. A magnet is secured to the bobber. The container can be driven in an oscillating motion. An external magnetic field is generated adjacent to the bobber. A magnetic field strength detector detects changes in the magnetic field as a result of movement of the bobber and magnet responsive to the oscillating motion of the container and clotting of the sample.

Such a new measuring system entails acceptability problems and uncertainties for a user. Moreover, that analysis device does not fit in existing measuring systems. Therefore new systems have to be completely designed.

All these modifications lead to a significant improvement of handling of modern thromboelastometers and thromboelastographs, however, no successful approach to develop a widely automated technique has been made since Hartert's invention 60 years ago. One of the two main reasons of that is the fact that the measurement requires two disposable parts (cup and pin) being moved in relation to each other and thus have to be reversibly attached to different parts of the measurement device. E.g. in FIG. 3, the probe pin 3 is attached to the shaft 6 and the cup 2 to the cup holder 12, respectively. The other main reason is that different tests are required to get comprehensive information of a current bleeding status of a patient. These different tests require different reagents which have to be mixed with the blood sample.

SUMMARY OF THE INVENTION

It is a problem underlying the presented invention to provide a cartridge device for a measuring system for measuring viscoelastic characteristics of a sample liquid, in particular a blood sample.

Directly connected to this invention is the problem to provide a corresponding measuring system for measuring viscoelastic characteristics of a sample liquid, in particular the coagulation characteristics of a blood sample liquid.

It is a further problem underlying the invention to provide a method for measuring viscoelastic characteristics of a sample liquid using said measuring system.

These problems are solved by the subject-matter of the independent claims. Preferred embodiments are set forth in the dependent claims.

In a first aspect, the present invention provides a cartridge device for a measuring system for measuring viscoelastic characteristics of a sample liquid, in particular a blood sample, comprising a cartridge body having at least one measurement cavity formed therein and having at least one probe element arranged in said at least one measurement cavity for performing a test on said sample liquid; and a cover being attachable on said cartridge body;

wherein said cover covers at least partially said at least one measurement cavity and forms a retaining element for retaining said probe element in a predetermined position within said at least one measurement cavity.

In a second aspect, the present invention provides a measuring system for measuring viscoelastic characteristics of a sample liquid, in particular a blood sample, comprising: at least one interface element; at least one shaft rotatably supported by the interface element to be rotated by drive means; at least one cartridge device fixed to the interface element for holding the sample liquid, the at least one cartridge device comprising a cartridge body with a cover and at least one probe element arranged in a measurement cavity formed in said cartridge body for cooperating with the at least one shaft; at least one detecting means cooperating with the shaft for measuring viscoelastic characteristics of the sample liquid; and control means to control the measuring system.

In a third aspect, the present invention provides a method for measuring viscoelastic characteristics of a sample liquid by means of said measuring system, comprising the following steps:

a) providing the cartridge device having at least one measurement cavity with at least one probe element arranged therein;

b) attaching the cartridge device to said interface element, said shaft being inserted into said probe element;

c) filling said measurement cavity of said cartridge device with sample liquid;

d) rotating said shaft in an oscillating motion around said rotation axis; and e) measuring viscoelastic characteristics of said sample liquid by detecting the rotation of said shaft by said detecting means.

In a preferred embodiment the probe element comprises a probe pin to cooperate with the sample liquid and a connector section for a connection to the measuring system. The connector section is formed e.g. as a bore extending within the probe element and comprises frictional connection means which can be e.g. clip means or a thread. An insertion guide facilitates an insertion of a part, in particular a shaft, of a measuring system. Thereby the shaft can be connected securely to the probe element.

The at least one measurement cavity can comprise bearing or supporting means for the probe element to align or hold the probe element prior to insertion of the shaft.

After the shaft has been inserted into the connector section, the shaft can be lifted to position the probe element at a working position.

In an alternative preferred embodiment the probe element is formed as a detachably fixed component part of the cover. An operator only has to attach the cartridge device to the measuring system the shaft being inserted into the probe element will detach the probe element from the cover and hold it securely in a position ready to carry out a measurement. Therefore the probe element comprises a fixing section for detachably fixing the probe element at fixing means of the cover.

After a measurement the cartridge device can be detached from the measuring system wherein the shaft is removed from the probe element. Then the probe element will seal the measurement cavity against the cover by means of e.g. a flange adapted to form a sealing. The cover retains the probe element within the measurement cavity.

It is preferred that the fixing means of the cover comprises clip means cooperating with corresponding clip means of the fixing section of the probe element.

In an alternative embodiment the fixing section of the probe element is integrally formed with the cover, the fixing means of the cover comprising a perforation.

The cover can be fixed on the cartridge body either by bonding or welding. In an alternative embodiment the cover is integrally formed with the cartridge body, e.g. made of a plastic material. It is also possible that the cover is made of a material which is different from the cartridge body. That can be done for example by two- or more-component-moulding.

In a further preferred embodiment the cartridge device further comprises at least one receiving cavity formed therein for receiving the sample liquid; at least one reagent cavity for holding at least one reagent; a ductwork connecting said cavities and the at least one measurement cavity; and at least one pump means connected to the ductwork for transporting the sample liquid from the at least one receiving cavity to the at least one measurement cavity by means of the ductwork, wherein the cover covers and at least partially forms said cavities and said ductwork and forms at least partially the pump means.

In a further embodiment the at least one reagent cavity is integrally formed with the pump means or/and with the at least one measurement cavity or/and with one or more of the ductworks. The reagent cavity can be formed as a deep cavity or just a small place where reagent can be deposited. Thus the sample liquid being pumped through the ductwork and the pump means into the measurement cavity can be mixed with the reagent.

The pump means comprise at least one valve for a directed flow of the sample liquid in order to direct the pumped liquid into the measurement cavity.

In another embodiment the reagent or an additional reagent can be stored in at least one reagent receptacle which can be opened by external means.

In a further embodiment the at least one reagent receptacle storing a reagent is integrated in the cover.

In another embodiment the at least one reagent receptacle comprises a bottom part which can be opened by external means to discharge the reagent into the ductwork and/or into one of the cavities. The receptacle can be adapted as a blister receptacle, for example.

The at least one reagent can be stored within the cartridge device in pulverized, solid or liquid form.

The cartridge device can be further provided with at least one reagent stored therein.

Filling in sample liquid can be done directly into the measurement cavity if no receiving cavity is provided. To this end the sample liquid can be injected through the cover via an opening or passage hole in the interface element or through a ductwork by an operator or by a control apparatus.

In case of a receiving cavity the sample liquid can be filled into the receiving cavity and be pumped by the pump means to the measuring cavity.

To fill in sample liquid, operate the pump means, add reagents and/or open the reagent receptacle the measuring system is equipped with a control apparatus. The control apparatus has means to access the pump means through a pump access formed as a passage of the interface element. Further the control apparatus can inject sample liquid through an inlet opening in the interface element into the receiving cavity. The control apparatus comprises also operating means to inject or to add reagents into the cartridge device as well as to open reagent receptacles.

Further features and advantages of the present invention will be evident from a description of embodiments with reference to the figures.

BRIEF DESCRIPTION OF THE DRAWINGS

The figures are showing the following:

FIG. 7b is a schematic drawing of the first embodiment of the probe element of

FIG. 7a within a measuring cavity of the first or a second embodiment of the cartridge device according to the invention before use.

FIG. 8a . . . c are technical drawings of the preferred probe element of FIG. 7a.

FIG. 9b is a sectional view B-B of the cartridge device of FIG. 9a.

FIG. 9c is a sectional view C-C of the cartridge device of FIG. 9a.

FIG. 9d is a sectional view D-D of the cartridge device of FIG. 9a.

FIG. 10a is a top view of the cartridge device of FIG. 9a.

FIG. 10b is a sectional view E-E of the cartridge device of FIG. 10a.

FIG. 11a is a sectional view of a pump means of the cartridge device of FIG. 9a.

FIG. 12 is a schematic top view of the pump means of FIG. 11a.

FIG. 13b is a top view of the measuring system of FIG. 13a.

DESCRIPTION OF EXEMPLARY EMBODIMENTS

Figure 1:
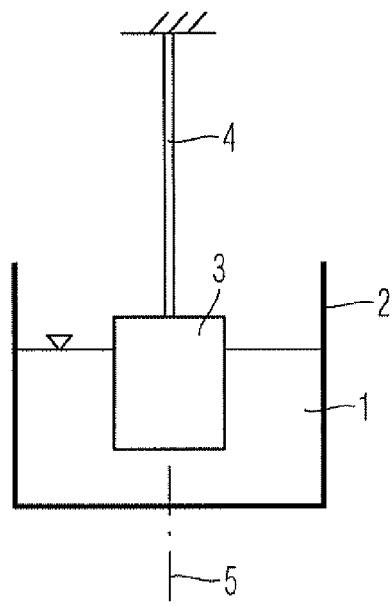
FIG. 1 is a schematic drawing of the principle of thromboelastography according to Hartert.
Figure 2:
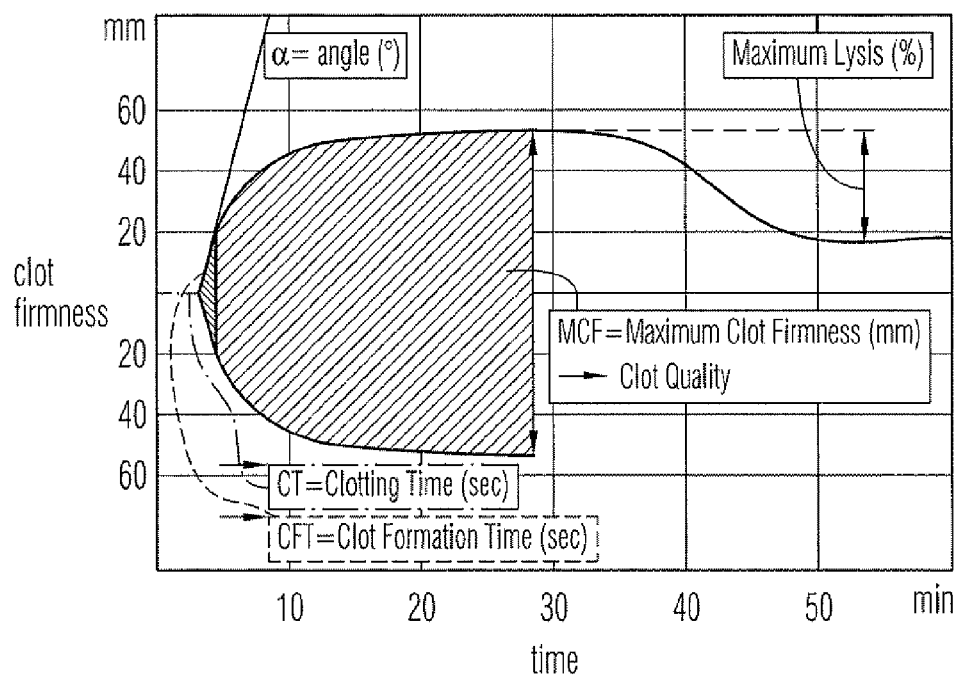
FIG. 2 is an exemplary diagram showing a typical thromboelastometric measurement.

Parts and components having same functions are depicted with same references.

Prior to a detailed description of the preferred embodiments the basic features and a basic practical implementation are summoned as follows. All embodiments refer to a cartridge device 50 (see FIG. 13c) which can be formed in a first embodiment (see FIGS. 4, 5 and 6), in a second embodiment (see FIGS. 7b, 7c and 15) or in a third embodiment (see FIGS. 9 to 10). The cartridge device 50 contains all parts coming into contact with a sample liquid 1 to be tested. These can be also reagents the sample liquid has to be mixed with for a measurement. The cartridge device 50 is part of a measuring system 40 (see FIG. 13c) to which the cartridge device 50 is attached before measurement. The measuring system 40 also comprises a control apparatus (not shown) which has been adapted to interact with the cartridge device 50 by electrical and/or mechanical means to control flow of sample liquid 1 (see FIG. 7c) and measurements as well as collect data. Furthermore this apparatus contains mechanical and electronic parts required for measurement, data analysis and user interaction. The present invention is not only suitable for thromboelastometry, thromboelastography and platelet aggregometry but also for other blood tests usually performed regarding surgery.

A first embodiment of a cartridge device 50 of the invention will be described with reference to FIGS. 4 and 5. The cartridge device 50 for the measuring system 40 for measuring medical relevant, e.g. viscoelastic, characteristics like coagulation or platelet function of a sample liquid 1, particularly a blood sample, comprises a receiving cavity 16 for receiving the sample liquid 1, pump means 18 for pumping the sample liquid, a reagent cavity 19 for storing a reagent 21, a measurement cavity 20 for measuring the sample liquid 1 and a ductwork connecting said cavities. The ductwork comprises an inlet duct 13 from the receiving cavity 16 to the pump means 18, an intermediate duct from the pump means 18 to the reagent cavity 19 and an outlet duct 15 from the reagent cavity 19 to the measurement cavity 20. In a variation said cavities and ducts can be arranged in different ways one of which is shown in FIG. 5, wherein pump means 18 and reagent cavity 19 are changed.

In this embodiment the receiving cavity 16 consists of a cavity within the cartridge device 50. The sample liquid 1 can be applied by means of a syringe, pipette etc, e.g. through a self sealing cap shown as a receiving cavity cover 33a in FIG. 10b. By operating the pump means 18, e.g. by means of the control apparatus mentioned above, the sample liquid is transported to the reagent cavity 19, where the reagent 21 required for measurement is mixed with the sample liquid 1. Further pumping the sample liquid 1 will transfer it into the measurement cavity 20 in which the measurement (described below) is carried out.

In an alternative embodiment the reagent cavity 19 is integral formed with the pump means 18 and/or with the measurement cavity 20 and/or with the ductwork. The transport of the sample liquid 1 can be controlled by said control apparatus.

Figure 6:
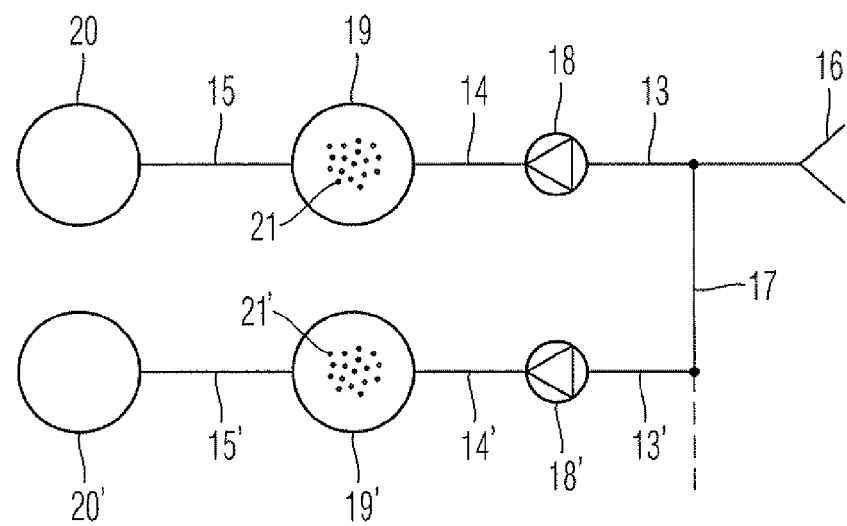
FIG. 6 is a schematic drawing of another variation of the first embodiment of the cartridge device according to the invention.

FIG. 6 shows another variation of the first embodiment. Two arrangements of FIG. 4 with only one receiving cavity 16 are arranged in parallel, wherein a first inlet duct 13 communicates with a second inlet duct 13' connected to second pump means 18'. A second intermediate duct 14' leads to a second reagent cavity 19' storing a second reagent 21'. A second outlet duct 15' connects the second reagent cavity 19' to the second measurement cavity 20'. FIG. 6 shows only one possible variation of a plurality of different arrangements easily imagined. The sample liquid 1 is shared among the arrangements in parallel.

Controlled by the external control apparatus the shared portions of the sample liquid 1 are mixed with different reagents 21, 21' during transport. It is apparent to a person skilled in the art that in order to achieve a maximum benefit for a user different types of tests can be combined in one cartridge device 50.

Figure 4:
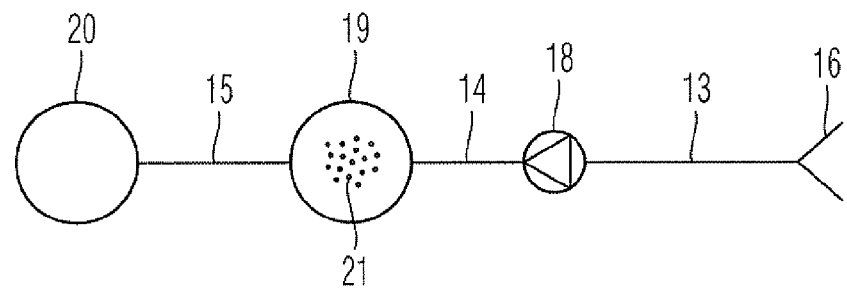
FIG. 4 is a schematic drawing of a first embodiment of a cartridge device according to the invention.
Figure 5:
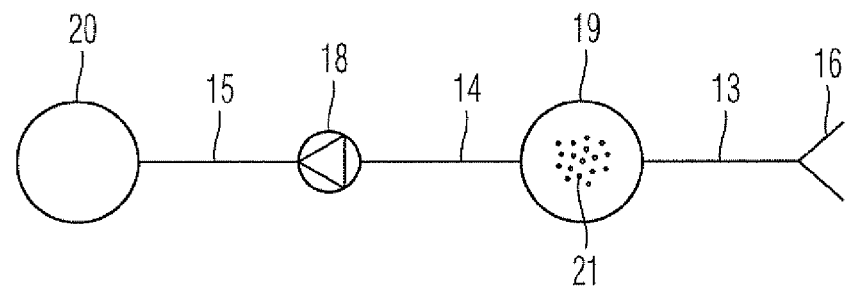
FIG. 5 is a schematic drawing of a variation of the first embodiment of the cartridge device according to the invention.

In a preferred embodiment the cartridge device 50 comprises four arrangements of FIG. 4 or 5 having 4 measurement cavities 20, 20'. Thus measurements can be done with different reagents on the same liquid sample or with same reagents as well to check plausibility.

Regarding e.g. blood coagulation there are different reagents available which activate or suppress different parts of the coagulation cascade. Pentapharm GmbH (Munich, Germany) for example amongst others provide tests for intrinsic and extrinsic activation of a blood sample (INTEM or EXTEM respectively), and also a test for extrinsic activation in which the thrombocyte function is suppressed by administration of cytochalasin D (FIBTEM). It is state of the art that it is possible by wise combination of such tests to be able to determine very precisely at which point within the coagulation cascade a problem occurs. This is of great importance in order to determine a proper medication. By comparison of the results on an EXTEM test of a pathologic sample to those of a FIBTEM test of the same sample it is possible to e.g. precisely determine if a coagulation disorder results from lack of fibrinogen or a malfunction of platelets. Generally, there are different typical medical scenarios in which coagulation disorders are very likely to occur. For example coagulation disorders occurring during liver transplantation are merely caused by lack of certain coagulation factors etc., while coagulation disorders during open heart surgery are most likely due to the influence of heparin. This means basically that different medical settings require different coagulation tests. Referring to FIG. 6 it is possible and worthwhile to provide different cartridge devices 50 for different typical operations. It is also possible to combine e.g. an INTEM, an EXTEM and a FIBTEM coagulation test with a platelet aggregometry test within one cartridge. Using such a cartridge the preparation of a measurement which provides almost overall information about the coagulation status of a patient merely requires the two steps of attaching the cartridge device 50 to the measuring system 40 with the external control apparatus and injecting the blood sample as one sample liquid 1. Considering the significance of more complex and time consuming preparation of several thromboelastography or thromboelastometry tests, it is evident that the invention is of great advantage for easier, safer and more accurate POC-tests.

It is important to note that the cartridge devices 50 of the described embodiments are suitable for different diagnostic tests like thromboelastometry, thromboelastography, platelet aggregometry and others. Depending on which type of test or tests the cartridge device 50 is designed for, there are different additional parts required which interact with the sample during measurement and/or an external control apparatus. Possible adaptations for thromboelastometry and platelet aggregometry are described below.

Figure 7A:
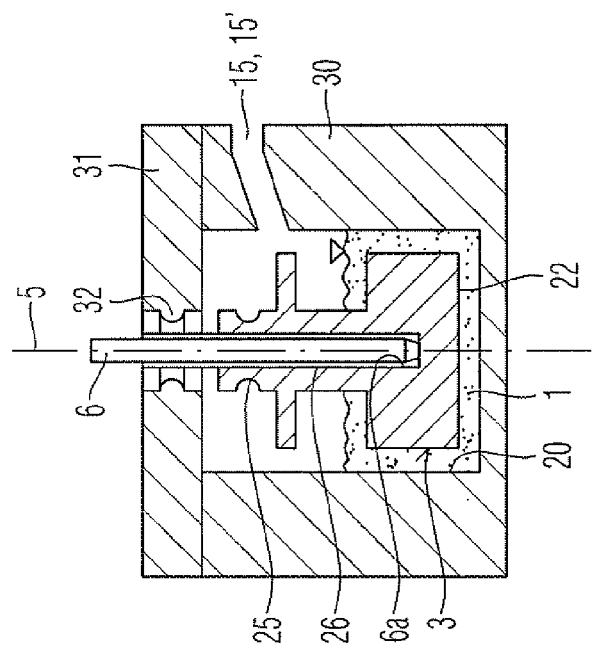
FIG. 7a is a schematic drawing of a first embodiment of a probe element.
Figure 7B:
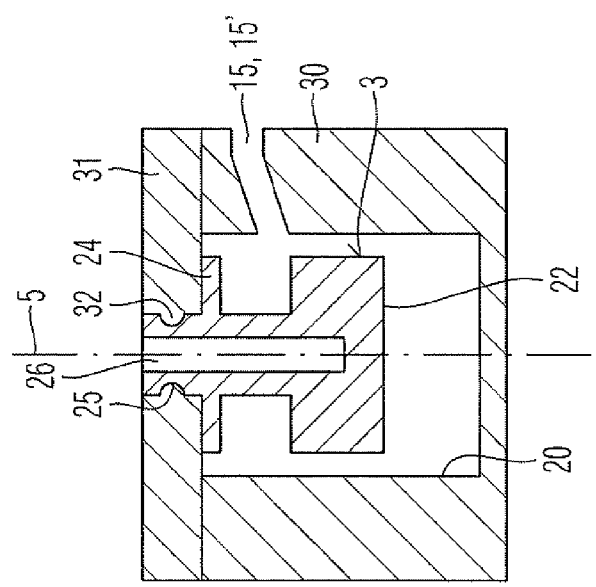
Figure 7C:
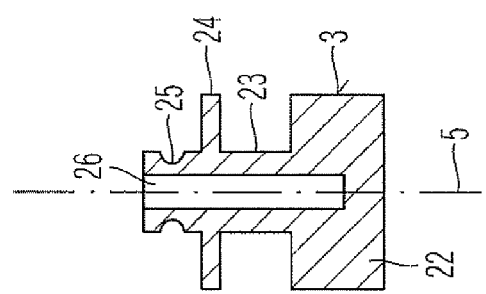
FIG. 7c is a schematic drawing of the first embodiment of the probe element of FIG. 7a within a measuring cavity of the first or the second embodiment of the cartridge device according to the invention in use.
Figure 10A:
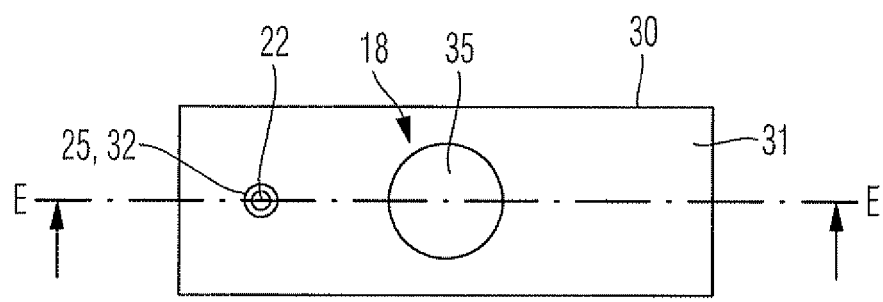
Figure 10B:
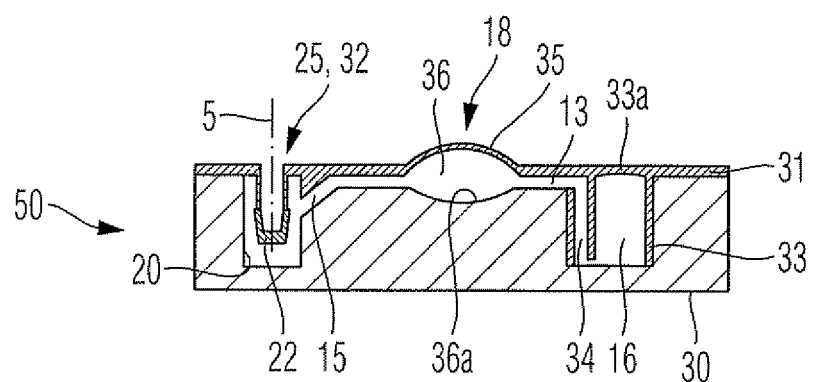
Figure 13A:
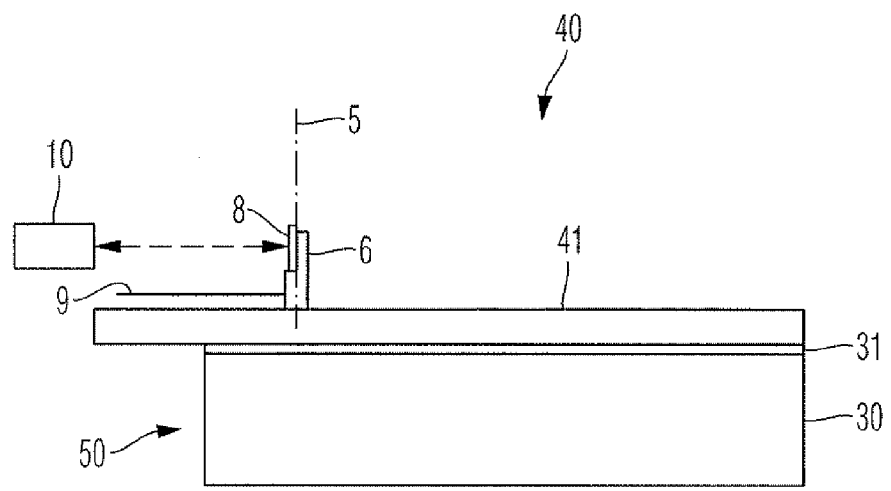
FIG. 13a is a side view of an embodiment of a measuring system according to the invention.
Figure 13B:
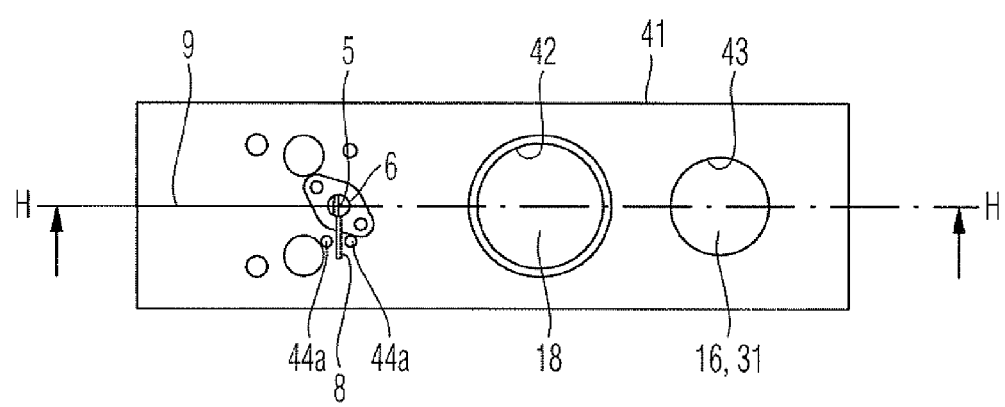
Figure 13C:
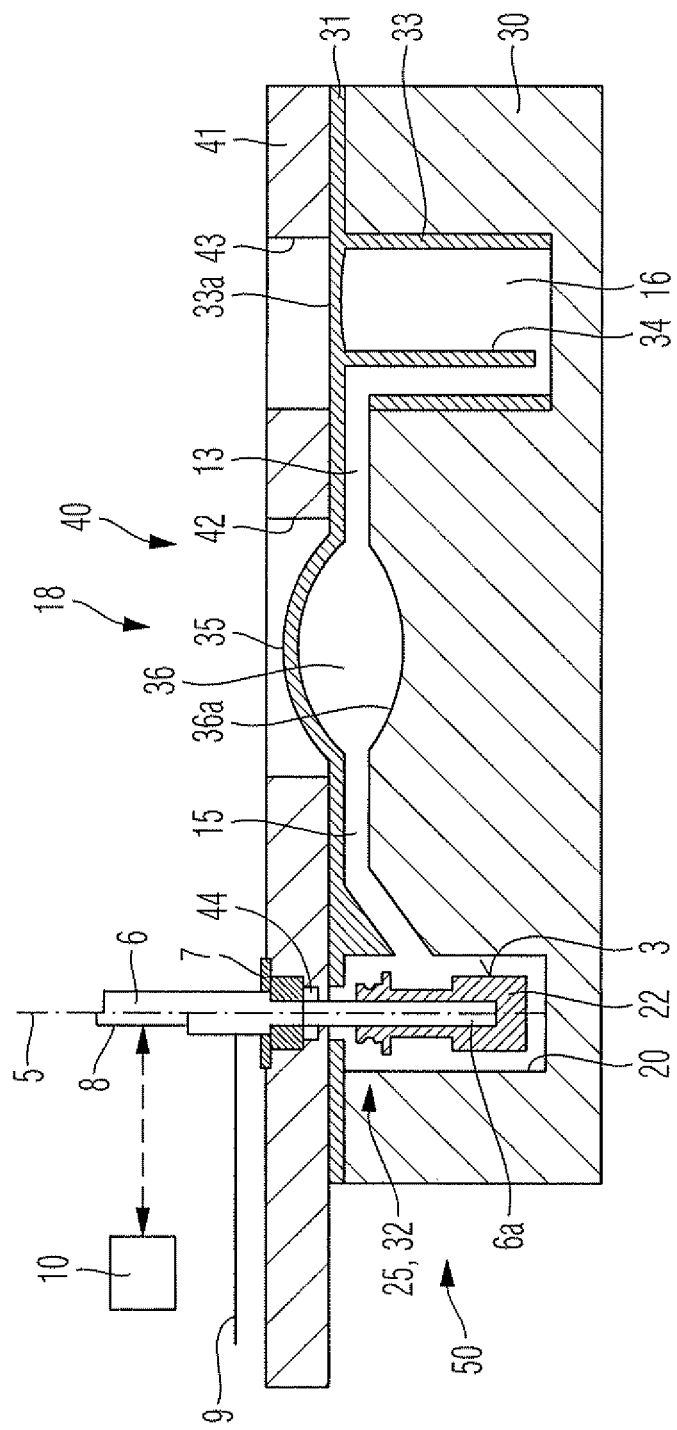
FIG. 13c is a sectional view H-H of the measuring system of FIG. 13b.

FIG. 7a is a schematic drawing of a first embodiment of a probe element 22 arranged in the measurement cavity 20 (see also FIGS. 10b and 13c). FIGS. 7b and 7c show a second embodiment of the cartridge device 50 in form of a cartridge body 30 which comprises only the measurement cavity 20. In the shown example this cavity 20 is accessible via a ductwork 15, 15' through a cavity wall. Alternatively the cavity 20 can be filled through a cover 31, e.g. by injection needles or the like.

Figure 3:
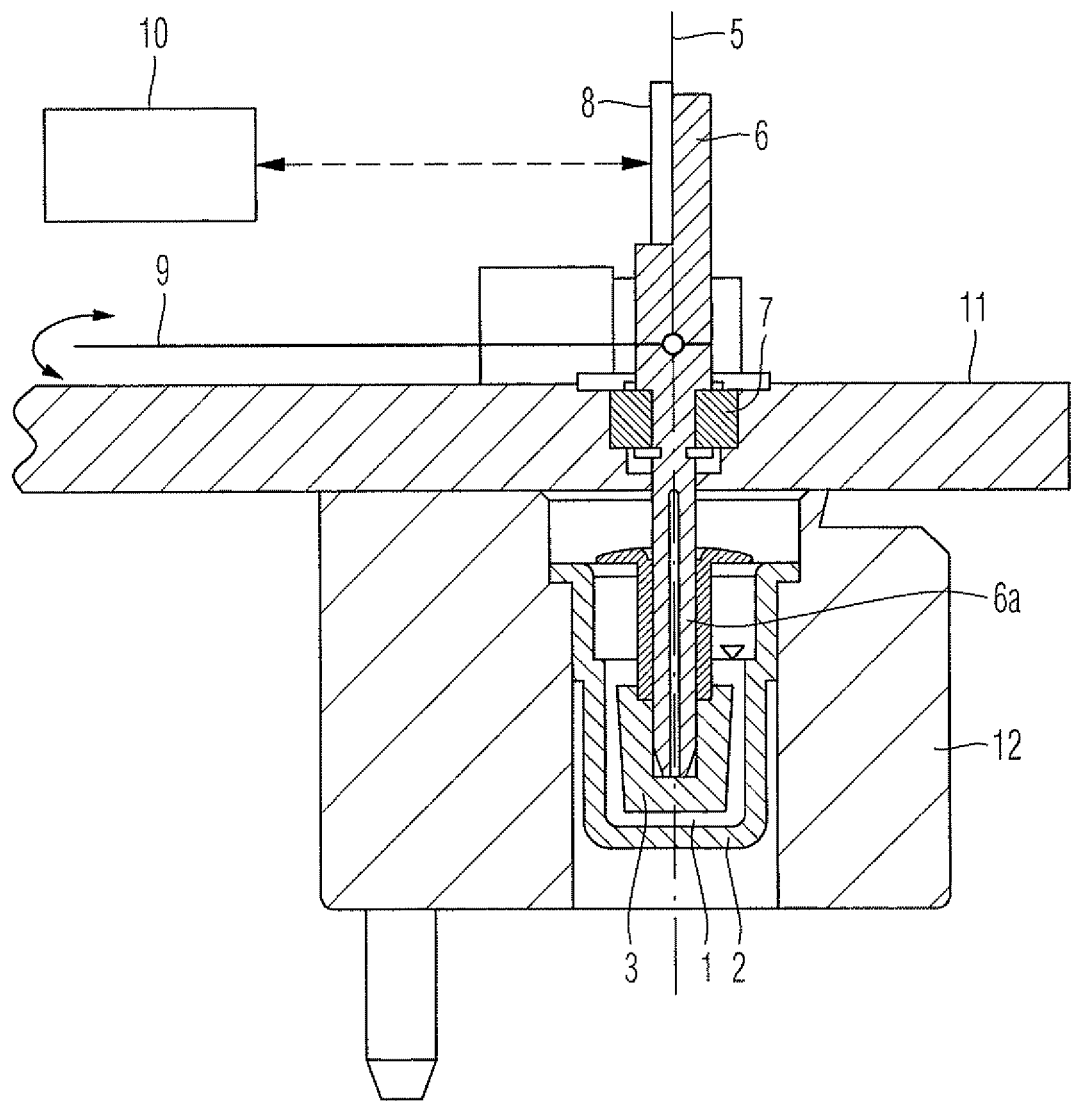
FIG. 3 is a schematic drawing of the thromboelastometry.

The probe element 22 comprises the probe pin 3 (see FIG. 1) which is connected to a flange 24 and a fixing section 25 via an intermediate section 23. The probe element 22 is formed as a rotational part and further comprises a connector section 26 formed as a bore extending within the probe element 22 along its longitudinal axis, which is the rotational axis 5 as well (see FIG. 3).

The probe element 22 is arranged in the measurement cavity 20 of the cartridge body 30 of the cartridge device 50 as shown in FIG. 7b. The measurement cavity 20 is covered by the cover 31 (see also FIGS. 10b and 13c). The cover 31 comprises an opening with fixing means 32 above the measurement cavity 20. The probe element 22 is arranged such that its fixing section 25 corresponding to the fixing means 32 engage with them. In this manner the probe element 22 is detachably fixed to the cover 31. The fixing means 32 in this example are equipped with a circular nose corresponding to a circular notch of the fixing section 25 of the probe element 22. Other fixing means e.g. clip means or the like are possible. The flange 24 is in contact to the inner side of the cover 31.

During attaching the cartridge device 50 to the measuring system 40 (see also FIG. 13c) the shaft 6 of the measuring system 40 (see FIG. 3 and FIGS. 13a . . . c) is inserted with its bottom portion, an insert section 6a, into the connector section 26. By insertion into the connector section 26 of the probe element 22 the probe element 22 will be detached from the cover 31 not before the insert section 6a is completely inserted in the connector section 26. Then the probe element 22 will be put into in a measuring position as shown in FIG. 7c and kept there. The insert section 6a of the shaft 6 is engaged with the connector section 26 of the probe element 22 e.g. by friction, clip means, thread or the like. In case of a thread the probe element 22 will be hold by the engagement with or perforation of the cover 31. The shaft 6 having a corresponding thread on its insert section 6a will be inserted into the connector section of the probe element 22 by rotation until the insert section 6a will be completely inserted into the connector section 26. Then the shaft 6 can be pushed down and/or rotated together with the fully engaged probe element 22 until the probe element 22 will be detached from the cover 31. FIG. 7c shows the sample liquid 1, which has been pumped into the measurement cavity 20. The probe pin 3 of the probe element 22 is immersed in the sample liquid 1. A measurement as described above can be carried out. After the measurement the cartridge device 50 is detached from the measuring system 40, wherein the shaft 6 is drawn up together with the probe element 22 against the cover 31. The insert section 6a of the shaft 6 will be drawn out of the connector section 26 of the probe element 22 the flange 24 thereof contacting and sealing the opening of the cover 31. Instead of a flange 24 the upper end of the probe element 22 can have a larger diameter than the opening in the cover 31. It is preferred that the insert section 6a of the shaft 6 and the measurement cavity 20, 20' are formed symmetrically.

It is also possible to insert the insert section 6a of the shaft 6 into the connector section 26 of the probe element 22 and push the probe element 22 down until its bottom contacts the bottom of the measurement cavity 20, 20' ensuring that the insert section 6a is completely inserted into the connector section 26. Then the shaft 6 will be moved up into the measuring resp. working position of the probe element 22 as shown in FIG. 7c.

Figure 8A:
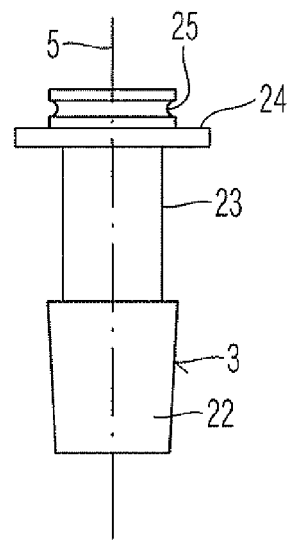
Figure 8B:
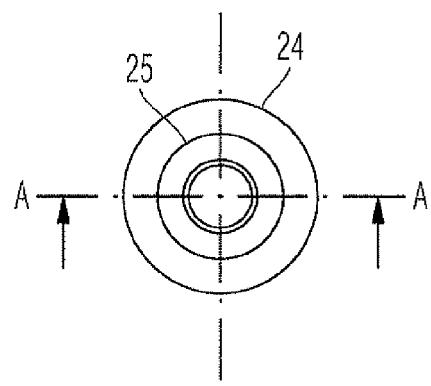
Figure 8C:
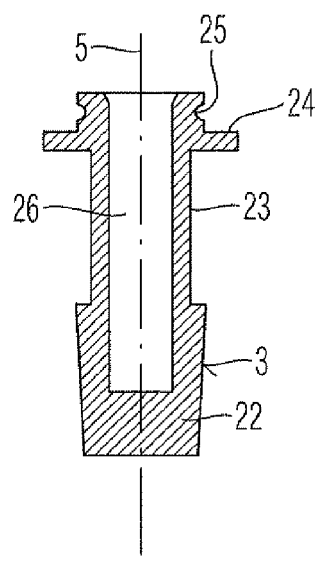

FIGS. 8a . . . c are technical drawings of a preferred embodiment of the probe element 22 of FIG. 7a. FIG. 8a shows a side view and FIG. 8b shows a top view of the probe element 22 parts of which have been described above regarding FIG. 7a. Finally, FIG. 8c illustrates a sectional view along rotational axis 5. The connector section 26 extends over more than about 75% of the length of the probe element 22.

Now a third embodiment of the cartridge device 50 will be described with reference to FIGS. 9a . . . d and FIGS. 10a . . . b.

Figure 9A:
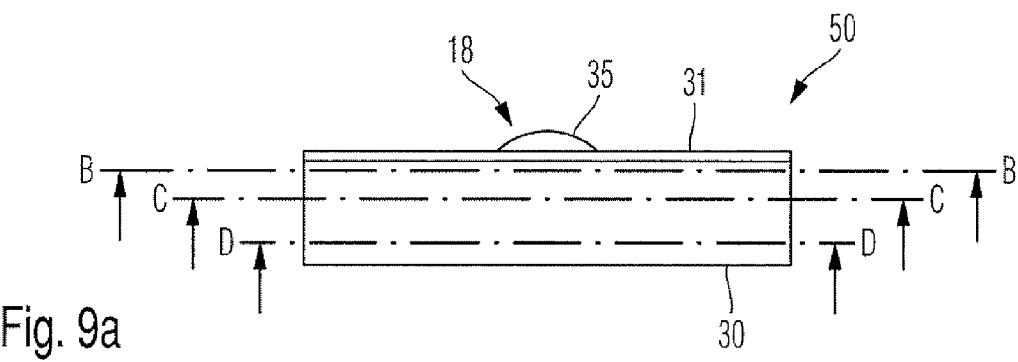
FIG. 9a is a side view of a third embodiment of a cartridge device according to the invention.
Figure 9B:
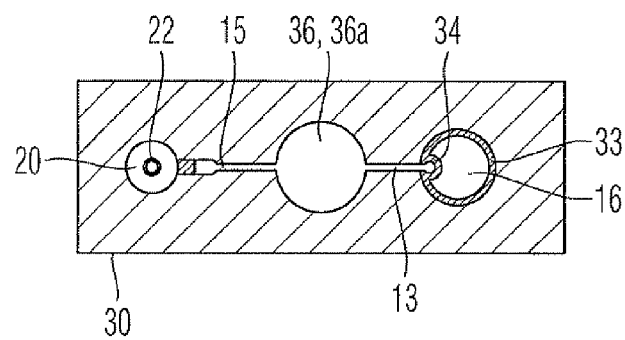
Figure 9C:
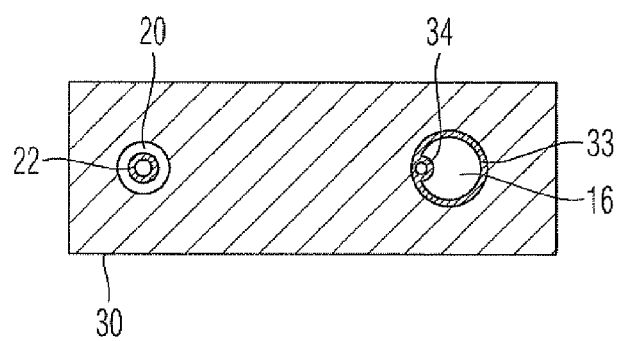
Figure 9D:
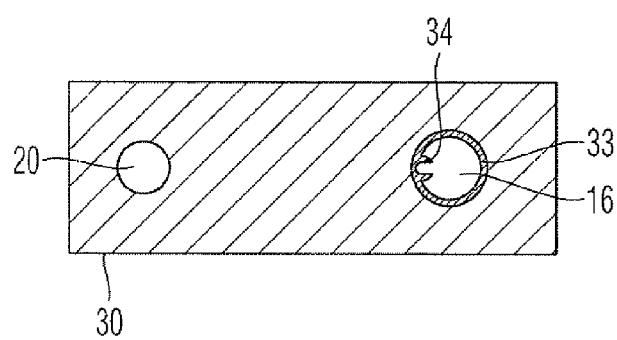

FIG. 9a is a side view of a second embodiment of a third embodiment of the cartridge device 50 according to the invention. FIG. 9b is a sectional view B-B of the cartridge device 50 of FIG. 9a. FIG. 9c is a sectional view C-C of the cartridge device of FIG. 9a. FIG. 9b is a sectional view D-D of the cartridge device of FIG. 9a. FIG. 10a is a top view of the cartridge device of FIG. 9a. FIG. 10b is a sectional view E-E of the cartridge device of FIG. 10a.

The cartridge device 50 of this example is equipped with the ductwork 13 and 15. The ducts are formed with an diameter of approximately 1 mm in this embodiment. The ductwork requires that the cartridge device 50 comprises two parts: the cartridge body 30 and the cover 31, which are glued or welded together to obtain a leak-proof device. The cartridge body 30 is relative rigid and the cover 31 is formed as an elastic part. So it is possible to integrate the pump means 18 into the cover 31. Moreover, the cover 31 covers the receiving cavity 16 with the receiving cavity cover 33a and forms a type of liner wall 33 and a separation wall 34 forming an inlet for the inlet duct 13 within the receiving cavity 16. The receiving cavity cover 33a might act as a self seal for injection of a sample liquid 1 by a syringe for example. The cover 31 forms top parts of the ductwork 13 an 15 and a cover of the measurement cavity 20 (see also FIGS. 7b . . . c). In this example the pump means 18 comprises a pump membrane 35 formed by the cover 31. The pump membrane 35 cooperates with a pump cavity 36 formed with a pump cavity bottom 36a in the cartridge body 30 below the pump membrane 35.

In this embodiment a reagent cavity 19, 19' is formed, e.g. by sections of the ductwork or/and the pump means 18, 18' in which the reagents can be stored resp. deposited, especially on the pump cavity bottom 36a, for example.

The pump means 18 will now be described with reference to FIGS. 11a . . . b and FIG. 12.

Figure 11A:
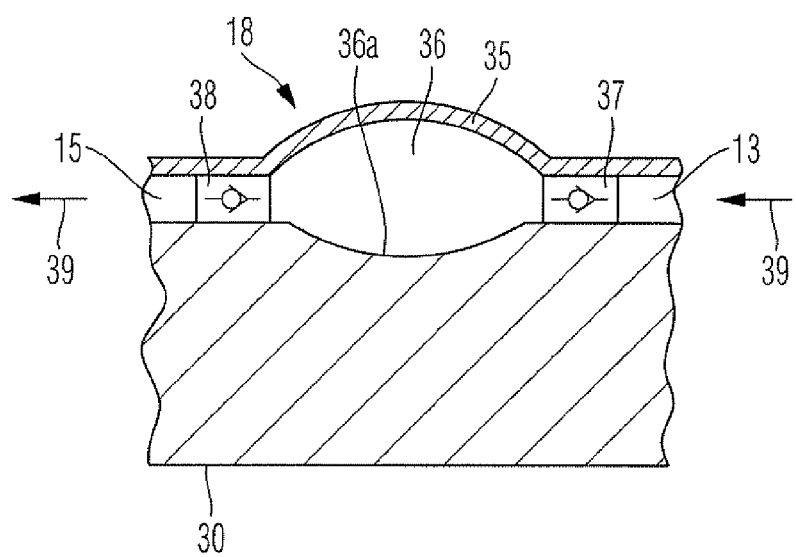
Figure 11B:
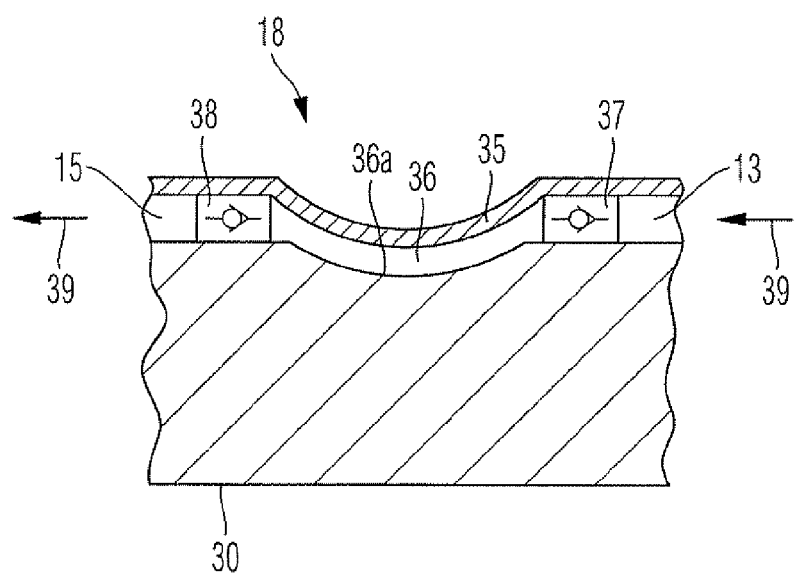
FIG. 11b is a sectional view of the pump means of FIG. 11a in operated position.
Figure 12:
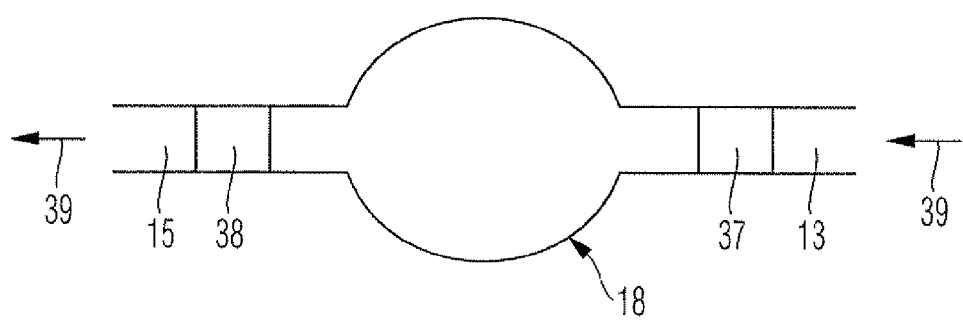

FIG. 11a is a sectional view of the pump means 18, 18' of the cartridge device 50, FIG. 11b is a sectional view of the pump means 18 of FIG. 11a in operated position, and FIG. 12 is a schematic top view of the pump means 18 of FIG. 11a.

In this example the pump cavity 36 is connected to the inlet duct 13 via an inlet valve 37 and to the outlet valve via an outlet valve 38. Actuation of the pump membrane 35 (shown in FIG. 11b in a working cycle) by an appropriate actuating means (not shown) of the control apparatus the pump means 18 will create a directed flow of the sample liquid 1 in a flow direction 39 depicted by the arrows. The pump membrane 35 being an integrated part of the cover 31 can be made of the cover material or a part made of another material integrally manufactured with the cover 31, e.g. two components manufacturing. The valves 37, 38 can be a type of non-return valve. FIG. 12 shows a top view of the pump means in a schematic way.

An external force exerted on the pump membrane 35 increase the pressure within the pump cavity 36 and opens outlet valve 38 and closes inlet valve 37. Releasing the external force the elastic pump membrane 35 returns into the position shown in FIG. 11a whereby outlet valve 38 will be closed and inlet valve 37 opened to let sample liquid 1 into the pump cavity 36. This mechanism is state of the art according to DE10135569. In context with the present invention the actuation means of the control apparatus activating the pump membrane 35 from outside has the advantage of strict separation between those parts coming into contact with the sample liquid 1 and the control apparatus. At the same time the total number of parts required for the cartridge device 50 being a disposable part as well is kept on a minimum.

Now the measuring system 40 according to the invention is described in an embodiment with reference to FIGS. 13a . . . c.

FIG. 13a is a side view of an embodiment of the measuring system 40, FIG. 13b is a top view of the measuring system 40 of FIG. 13a, and FIG. 13c is a sectional view H-H of the measuring system 40 of FIG. 13b.

The measuring system 40 comprises an interface element 41 to which the cartridge device 50 is attached and fixed. The interface element 41 is shown in FIGS. 13a to 13c in way of example as a base plate. The function of the interface element 41 is to support the shaft 6 and to maintain its position and thus the position of the probe element 22 fixed to the insert section 6a in a measurement position. The interface element 41 can be connected to the whole cover 31 as shown in FIG. 13a to 13c or only to parts of the cover 31, e.g. surrounding the rotation axis 5. The shaft 6 is rotatable supported in a bearing 7 within a shaft passage 44 (FIG. 13c) and can be rotated around the rotation axis 5 (see also FIG. 3) by driving the spring 9 via driving means (not shown). The detecting means 10 cooperate with the mirror 8 fixed on the shaft 3, also shown in FIG. 3. The control apparatus mentioned above is not shown as well, but easy to imagine. Its actuation and/or operating means can access the pump means 18 through an opening pump access 42 in the interface element 41. The receiving cavity 16 is accessible through another inlet opening 43. These and other different passages or passage ways of the interface element 41 to have access to the cartridge device 50 and/or its cover 31 are illustrated by FIG. 13b as a top view of the measuring system 40 of FIG. 13a. Passage holes 44a are arranged next to the rotational axis 5 to form an access to the cover 31 above the measurement cavity 20, 20', e.g. for injection of liquid sample or reagents. Additional access passage holes can be arranged in the interface element 41, e.g. above the ductwork to access said ductwork.

FIG. 13c illustrates a sectional view H-H of FIG. 13b showing the mounted cartridge device 50 and the measuring system 40. The shaft 6 with its insert section 6a is inserted into the probe element 22 and keeps it in a measurement position as mentioned above. This embodiment comprises only one measurement cavity 20, but it is apparent to a person skilled in the art that modifications and combinations of the invention can be carried out in different ways.

Figure 14:
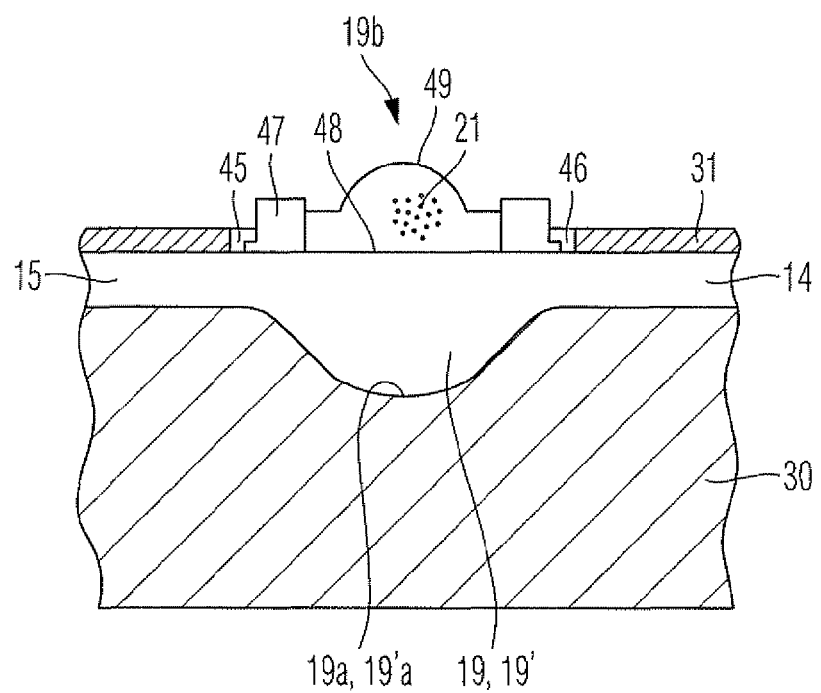
FIG. 14 is a sectional view of a reagent receptacle of a third embodiment of the cartridge device according to the invention.

Thus it is possible to e.g. arrange a reagent receptacle 19b in a blister receptacle e.g. as shown in FIG. 14 which is a sectional view of the reagent receptacle 19b of a third embodiment of the cartridge device 50 according to the invention. The receptacle 19b contains reagent 21 hold within a chamber defined by a blister cover 49, a bottom part 48 and a frame 47 hold in a retaining ring 46 within an reagent cover opening 45 in the cover 31 above the reagent cavity 19, 19' with a reagent cavity bottom 19a, 19a'. Upon exertion of a force by the control apparatus onto the blister cover 49 the bottom part 48 will open and discharge the reagent 21 into the reagent cavity 19, 19'. The receptacle 19b can be fixed to the cover by e.g. clip means as depicted. The frame 47 can be a reinforced ring. The blister cover 49 is reinforced so that it will not break when a force is exerted on it. Thus the leak-tightness of the cartridge device 50 will be ensured. In this way a unitized construction system can be made, wherein the respective reagents can be easily integrated into the cartridge device 50. It is also advantageous that the reagents can be designed as a small component being cooled resp. transported and supplied easily.

It is also possible to insert reagent receptacles into provided cavities being connected to the ductwork. The reagents can be designed as globules with an appropriate diameter so that they cannot flow through openings into the ductwork before being dissolved by the sample liquid.

Figure 15:
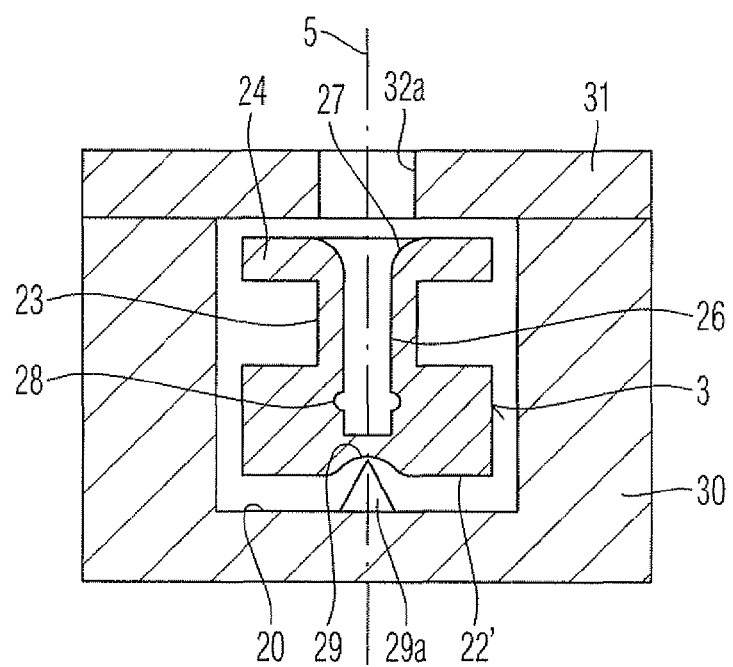
FIG. 15 is a schematic drawing of a second embodiment of the probe element.

FIG. 15 is a schematic drawing of a second embodiment of a probe element 22'. The probe element 22' is arranged in the measurement cavity 20. The probe pin 3 is provided with a dimple 29 at its bottom side. The dimple 29 forms with a nose 29a a toe bearing to support the probe element 22'. The probe element 22' is similar to the probe element 22 of FIG. 7a, but has no fixing section 25, only the flange 24. The connector section 26 comprises a top end formed with an insertion guide 27 for the insertion section 6a of the shaft. The probe element 22' is hold in the measurement cavity 20 in a specific manner so that the insertion section 6a of the shaft 6 can be inserted easily through an opening 32a of the cover 31 which has no fixing means. The insertion section 6a can engage with a groove 28 inside the connector section 26 of the probe element 22'. After that engagement which is supported by the toe bearing the shaft 6 will be drawn up together with the probe element 22' in the measuring position. It is a matter of fact that other engagement means can be used.

LIST OF REFERENCE NUMERALS

1 Sample liquid
2 Cup
3 Probe pin
4 Torsion wire
5 Rotation axis
6 Shaft
6a Insert section
7 Bearing
8 Mirror
9 Spring
10 Detecting means
11 Base plate
12 Cup holder
13, 13' Inlet duct
14, 14' Intermediate duct
15, 15' Outlet duct
16, 16' Receiving cavity
17 Branch duct
18, 18' Pump means
19, 19' Reagent cavity
19a, 19'a Reagent cavity bottom
19b Reagent receptacle
20, 20' Measurement cavity
21, 21' Reagent
22, 22' Probe element
23 Intermediate section
24 Flange
25 Fixing section
26 Connector section
27 Insertion guide
28 Groove
29 Dimple
29a Nose
30 Cartridge body
31 Cover
32 Fixing means
32a Opening
33 Wall
33a Receiving cavity cover
34 Separation wall
35 Pump membrane
36 Pump cavity
36a Pump cavity bottom
37 Inlet valve
38 Outlet valve
39 Flow direction
40 Measuring system
41 Interface element
42 Pump access
43 Inlet opening
44 Shaft passage
44a Passage hole
45 Reagent cover opening
46 Retaining ring
47 Frame
48 Bottom foil
49 Blister cover
50 Cartridge device

The invention claimed is:

1. A cartridge device for a measuring system for measuring viscoelastic characteristics of a blood sample, comprising:
a cartridge body having a plurality of blood testing cavities for receiving a portion of the blood sample, wherein the cartridge body retains a respective probe element in each of said blood testing cavities for measuring viscoelastic characteristics of the blood sample;
each respective probe element including: a lower head portion configured to engage with the portion of the blood sample in its corresponding blood testing cavity, and an upper connector section positioned proximate an upper rim of its corresponding blood testing cavity; and
wherein the upper connector section each respective probe element is positioned to mate with a corresponding shaft of a measuring system while the respective probe element is retained within its corresponding blood testing cavity such that the respective probe element is adjustable from a first position in which the lower head portion contacts a bottom of its corresponding blood testing cavity to a predetermined working position in which the lower head portion is spaced apart from the bottom of its corresponding blood testing cavity.

2. The cartridge device of claim 1, wherein each respective probe element is movable within its corresponding blood testing cavity for measuring viscoelastic characteristics of the portion of the blood sample.

3. The cartridge device of claim 1, wherein a cover is provided on said cartridge body.

4. The cartridge device of claim 3, wherein said cover at least partially covers each of said blood testing cavities.

5. The cartridge device of claim 3, wherein said cover forms a retaining element for retaining each respective probe element in a predetermined position within said at least one blood testing cavity, and wherein the probe element comprises sealing means for sealing the blood testing cavity against the cover.

6. A measuring system for measuring viscoelastic characteristics of a blood sample using at least one cartridge device according to claim 1, comprising:
at least one interface element;
at least one shaft rotatably supported by said interface element to be rotated by drive means;
at least one cartridge device according to claim 1 fixed to said interface element for holding said sample liquid, at least one respective probe element of said at least one cartridge device cooperating with said at least one shaft;
at least one detecting means cooperating with said shaft for measuring viscoelastic characteristics of a portion of said blood sample in contact with said at least respective probe element; and
control means to control said measuring system.

7. The measuring system of claim 6, wherein the respective probe element is movable within its corresponding blood testing cavity of the cartridge device for measuring viscoelastic characteristics of the portion of the blood sample.

8. A cartridge device for use with a blood coagulation measuring system, comprising:
a plurality of blood testing chambers for receiving a portion of a blood sample to measure blood coagulation characteristics;
a movable pin element positioned in each of the blood testing chambers, each movable pin element including: a lower head portion configured to engage with the portion of the blood sample in its corresponding blood testing chamber, and an upper connector section positioned proximate an upper rim of its corresponding blood testing cavity; and wherein the upper connector section each respective movable pin element is positioned to mate with a corresponding shaft of a measuring system while the respective movable pin element is retained within its corresponding blood testing cavity such that the respective movable pin element is adjustable from a first position in which the lower head portion contacts a bottom of its corresponding blood testing cavity to a predetermined working position in which the lower head portion is spaced apart from the bottom of its corresponding blood testing cavity.

9. The cartridge device of claim 8, further comprising a cartridge body that defines the plurality of blood testing chambers and that also defines corresponding ductwork for transporting at least some of the blood sample to each corresponding blood testing chamber.

10. The cartridge device of claim 9, further comprising a blood sample receiver portion, wherein the corresponding ductwork for each of the blood testing chambers is connected in parallel to the blood sample receiver portion.

11. The cartridge device of claim 10, wherein the blood sample receive portion comprises a self-sealing cover configured to receive a supply of the blood sample via a syringe or pipette.

12. The cartridge device of claim 9, wherein the cartridge body also defines a reagent chamber corresponding to each of the blood testing chambers, each reagent chamber including a reagent configured to mixed with the portion of the blood sample before at least some of the blood sample is transported via the ductwork into the corresponding blood testing chamber.

13. The cartridge device of claim 12, wherein each of the reagent chambers contains a different reagent so that each of the blood testing chambers receives a corresponding portion of the blood sample mixed with the different reagent.

14. The cartridge device of claim 13, further comprising a blood sample receiver portion that is connected via a first ductwork to a first reagent chamber and a first blood testing chamber and that is connected via a second ductwork to a second reagent chamber and a second blood testing chamber, wherein the first ductwork, the first reagent chamber, and the first blood testing chamber are connected to the blood sample receive portion in parallel to the second ductwork, the second reagent chamber, and the second blood testing chamber.

15. The cartridge device of claim 13, further comprising an inlet valve positioned along an input to each respective reagent chamber, and an outlet valve positioned along an output to each respective reagent chamber.

16. The cartridge device of claim 15, wherein the different reagent for each reagent chamber comprises reagent globules configured to dissolve in the respective portion of the blood sample.

17. The cartridge device of claim 6, wherein the upper connector section of each movable pin element positioned in each of the blood testing chambers is configured to mate with and releasably mount to a tip of the shaft of the measuring system.

18. The cartridge device of claim 17, wherein the upper connector section of each movable pin element is configured to friction fit with the tip of the shaft of the measuring system.

* * * * *